(12) United States Patent
Masuda et al.

(10) Patent No.: US 9,586,036 B2
(45) Date of Patent: Mar. 7, 2017

(54) MEDICAL CONNECTOR

(71) Applicant: NIPRO CORPORATION, Osaka (JP)

(72) Inventors: Takuya Masuda, Osaka (JP); Akihiko Ishizaki, Osaka (JP)

(73) Assignee: Nipro Corporation, Osaka (JP)

( * ) Notice: Subject to any disclaimer, the term of this patent is extended or adjusted under 35 U.S.C. 154(b) by 182 days.

(21) Appl. No.: 14/174,427

(22) Filed: Feb. 6, 2014

(65) Prior Publication Data

US 2014/0155837 A1    Jun. 5, 2014

Related U.S. Application Data

(62) Division of application No. 12/155,431, filed on Jun. 4, 2008, now Pat. No. 9,044,585.

(30) Foreign Application Priority Data

Jun. 5, 2007  (JP) ................................ 2007-149133

(51) Int. Cl.
*A61M 5/00*       (2006.01)
*A61M 39/22*      (2006.01)
(Continued)

(52) U.S. Cl.
CPC .......... *A61M 39/22* (2013.01); *A61M 39/045* (2013.01); *A61M 39/10* (2013.01);
(Continued)

(58) Field of Classification Search
CPC ..... A61M 39/10; A61M 39/22; A61M 39/045
(Continued)

(56) References Cited

U.S. PATENT DOCUMENTS 3,751,049 A    8/1973    Busby et al. ................. 277/382
4,219,912 A    9/1980    Adams .......................... 128/214
(Continued)

FOREIGN PATENT DOCUMENTS

JP    2-01275 A    1/1990
JP    2-502976     9/1990
(Continued)

OTHER PUBLICATIONS

Office Action dated Jun. 8, 2015, in Japanese Patent Application No. 2014-159240 and partial English translation.
(Continued)

*Primary Examiner* — Edelmira Bosques
(74) *Attorney, Agent, or Firm* — Kubovcik & Kubovcik

(57) ABSTRACT

A medical connector having a substantially cylindrical shape, a first upper end for receiving a male luer, and a second lower end, and including:
  a disc shaped valve member arranged at the first upper end and having an uppermost surface and a lowermost surface, a slit formed at a center portion thereof, an upper groove formed in a circumferential edge portion of the uppermost surface, and a lower groove formed in a circumferential edge portion of the lowermost surface;
  a housing with a pedestal for supporting the disc shaped valve member;
  a protrusion projecting upwardly from the pedestal and being arranged in the lower groove; and
  an annular ring member disposed on the circumferential edge portion of the uppermost surface, and having a claw portion projecting downwardly and being arranged in the upper groove on the uppermost surface of the valve member.

5 Claims, 2 Drawing Sheets

(51) Int. Cl.
   *A61M 39/04* (2006.01)
   *A61M 39/10* (2006.01)
   *A61M 39/26* (2006.01)

(52) U.S. Cl.
   CPC ..... *A61M 39/26* (2013.01); *A61M 2039/1033* (2013.01); *A61M 2039/1072* (2013.01); *A61M 2039/1083* (2013.01); *A61M 2039/1088* (2013.01); *Y10T 29/49826* (2015.01)

(58) Field of Classification Search
   USPC ....................................................... 604/246
   See application file for complete search history.

(56) References Cited

U.S. PATENT DOCUMENTS

| | | | |
|---|---|---|---|
| 5,033,476 A | 7/1991 | Kasai | 600/577 |
| 5,178,607 A | 1/1993 | Lynn et al. | 604/86 |
| 5,279,571 A | 1/1994 | Larkin | 604/167.02 |
| 5,400,500 A | 3/1995 | Behnke et al. | 29/785 |
| 5,515,705 A | 5/1996 | Weldon et al. | 72/19.1 |
| 5,591,137 A | 1/1997 | Stevens | 604/296 |
| 6,357,618 B1 | 3/2002 | Kloess et al. | 220/562 |
| 6,371,319 B2 | 4/2002 | Yeaton et al. | 215/352 |
| 2002/0193752 A1 | 12/2002 | Lynn | 604/249 |
| 2004/0171993 A1 | 9/2004 | Bonaldo | 604/248 |
| 2006/0184140 A1 | 8/2006 | Okiyama | 604/249 |
| 2007/0112311 A1* | 5/2007 | Harding | A61M 39/045 604/246 |
| 2007/0238337 A1 | 10/2007 | Kimball et al. | 439/157 |

FOREIGN PATENT DOCUMENTS

| | | |
|---|---|---|
| JP | 4-88942 U | 8/1992 |
| JP | 7-505064 | 6/1995 |
| JP | H8-057058 A | 3/1996 |
| JP | 10-323397 | 12/1998 |
| JP | 11-197254 | 7/1999 |
| JP | 2003-290362 A | 10/2003 |
| JP | 2005-021503 A | 1/2005 |
| JP | 2006-102255 A | 4/2006 |
| JP | 2009-011820 A | 1/2009 |
| WO | 89/06553 | 7/1989 |
| WO | 91/07206 | 5/1991 |
| WO | 93/11828 | 6/1993 |
| WO | 2005/004973 A1 | 1/2005 |
| WO | 2006/103074 | 10/2006 |

OTHER PUBLICATIONS

Office Action dated Jan. 5, 2015, issued in related Japanese Patent Appln. No. 2013-119801 (with partial English language translation).

Office Action dated Jun. 6, 2014, issued in corresponding Japanese Patent Appln. No. 2013-119801.

Office Action issued Nov. 14, 2016, in JP Application No. 2015-211093 (with English language translation).

Office Action issued Nov. 14, 2016, in JP Application No. 2015-211097 (with English language translation).

\* cited by examiner

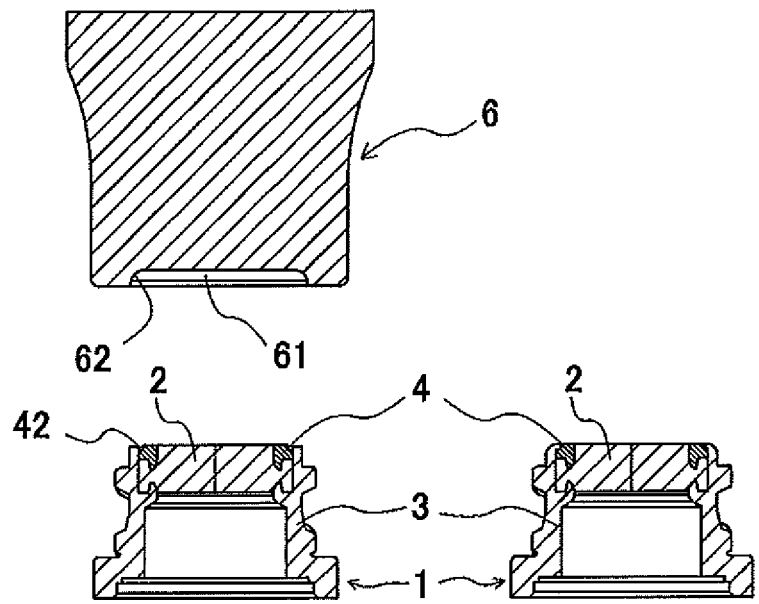
Fig. 4A    Fig. 4B
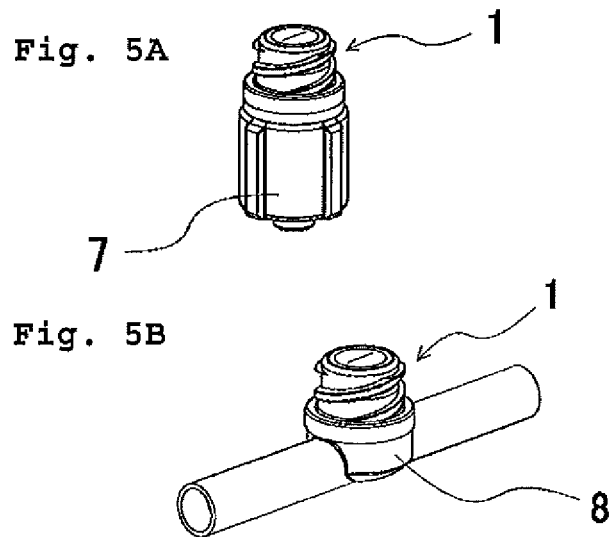
Fig. 5A
Fig. 5B
Fig. 5C

MEDICAL CONNECTOR

TECHNICAL FIELD OF THE INVENTION

The present invention relates to a medical connector capable of allowing a connection tool with a luer lock connector to be connected thereto upon mixing/injecting medicinal solution into an infusion route, or path or drawing out body fluid therethrough.

BACKGROUND OF THE INVENTION

In general, a medical connector, to which a medical connection tool such as a syringe or a luer lock connector can be connected, is disposed in an infusion route in order to mix and inject medicinal solution into the infusion route or to draw out body fluid therethrough. As the medical connector, there are known a cylindrical connector called a mechanical valve type in which a bellows cylindrical rubber valve with a spike built in the center portion thereof (see, for example, Japanese Patent Laid-Open No. 7-505064 or Japanese Patent Laid-Open No. 10-323397) and a connector called a split septum type which comprises a housing provided with a disc shaped valve (see, for example, Japanese Patent Laid-Open No. 11-197254).

The mechanical valve-type connector is configured to internally communicate the connection tool with the infusion route in such a manner that a male luer of a connection tool is inserted into an opening of the connector while pushing a rubber valve and then, a slit of the distal end portion of the rubber valve is opened by the spike at the center portion. Although the mechanical valve-type connector is formed into a cylindrical shape so as to be connected to the luer lock connector, manufacturing cost increases because the shape of the rubber valve is complicated.

Meanwhile, the split septum-type connector is a connector formed by a housing to which the disc shaped valve is fixed, and manufacturing cost decreases because the shape is simple. The split septum-type connector is configured to allow the infusion route to communicate with the connection tool in such a manner that the male luer of the connection tool is directly inserted into the slit of the disc shaped valve to open the slit. Accordingly, in order to maintain resealing performance of the slit, the disc shaped valve is fixed to the inside of the housing so that an elastic repulsive force is large.

In the past, in order to fix the disc shaped valve, a swaging process has been used (see, for instance, PCT Japanese Translation Patent Publication No. 2-502976). The fixation method is carried out in such a manner that a valve is inserted into a cylindrical housing and then, the upper end portion of the housing is deformed inward by the swaging process to fix the valve thereto. However, in such a fixation method, it is difficult to control the deformed part and to stably fix the disc shaped valve. In addition, the upper surface of the disc shaped valve is not flush with the upper surface of the housing, and thus a stepped portion is formed therebetween. When the stepped portion is formed between the upper surfaces of the disc shaped valve and the housing, it is not possible to sufficiently disinfect the upper surfaces before using the connector, and thus germs may be mixed with the fluid in the infusion route.

For this reason, in order to fix the disc shaped valve to the housing, for instance, a connector disclosed in Japanese Patent Laid-Open No. 11-197254 is configured such that a housing of which the upper end portion is deformed inward is disposed so as to cover the valve from the upside and then a holder member is used to fix the housing. With such a configuration, although a stepped portion is not formed on the upper surface of the connector, the shape becomes complicated because the number of components increases. In addition, since the outer diameter of the connector itself becomes large, it is not possible to carry out the connection operation of the luer lock connector in which a female screw is formed on the outer circumference of the male luer. Accordingly, when a connection operation of the luer lock connector is carried out, it is necessary to use an exclusive connector, thereby deteriorating the merit that the shape of the split septum-type connector is simple.

DISCLOSURE OF THE INVENTION

An object of the invention is therefore to provide a medical connector capable of allowing a luer lock connector to be connected thereto without using an exclusive connector, in which the shape or the assembling operation is not complicated and a stepped portion is not formed between the upper surfaces of the valve and the housing.

The inventors have carefully studied the above-described problems and then found out that the assembling operation can be easily carried out without a stepped portion formed between the upper surfaces of the valve member and the housing in such a manner that the upper end portion of the housing is not directly subjected to the swaging process, but the annular ring member disposed on the upper surface of the disc shaped valve member and the upper end portion of the housing are subjected to the swaging process. Accordingly, the inventors have found out that the connection operation of the luer lock connector can be carried out without using an exclusive connector or complicating the shape thereof because the valve member is firmly fixed to the housing, thereby developing the invention.

According to Aspect 1 of the invention, there is provided a medical connector including: a disc shaped valve member which has a slit formed at a center portion thereof; a housing with a substantially cylindrical shape which sandwiches a circumferential edge portion of the valve member; and an annular ring member which is disposed on an upper circumferential edge of the valve member other than the center portion thereof, wherein the housing has a pedestal which is formed in an inner circumferential surface thereof so as to protrude inward, the valve member being placed on the pedestal, and wherein the valve member is fixed to the inside of the housing by allowing the ring member and the housing to be joined to each other by a swaging process after the valve member is placed on the pedestal in the housing.

In the medical connector according to Aspect 1, an annular groove is formed in an upper surface of the valve member and the ring member is disposed in the annular groove of the valve member, so that the upper surface of the valve member is flush with an upper surface of the ring member.

In the medical connector according to Aspect 1 or 2, a concave portion is formed in an outer circumferential edge of the upper surface of the ring member in advance and an upper end portion of the housing which is melted by the swaging process flows into the concave portion, so that the upper surfaces of the housing, the ring member, and the valve member are flush with one another.

In the medical connector according to Aspect 1 or 2, a screw portion is formed in an outer circumferential surface of the housing so as to be screw-connected to a luer lock connector.

According to the present invention there is provided a method for producing the medical connector comprising;

preparing a disc shaped valve member which has a slit formed at a center portion thereof, a housing with a substantially cylindrical shape which sandwiches a circumferential edge portion of the valve member; and an annular ring member which is disposed on an upper circumferential edge of the valve member other than the center portion thereof, wherein the housing has a pedestal which is formed in an inner circumferential surface of the housing so as to protrude inward, placing the valve member on the pedestal, and joining the annular ring member to an upper portion of the housing by a swaging process so as to fix the valve member in the housing.

In the medical connector according to the invention, since the ring member is joined to the upper end portion of the housing by the swaging process in a state that the annular ring member is disposed on the upper surface of the valve member, it is possible to firmly fix the valve member to the inside of the housing without complicating the shape or the assembling operation. In addition, since the ring member is disposed on the upper surface of the valve member so that the upper surface of the valve member is flush with the upper surface of the ring member, it is possible to more surely prevent a stepped portion from being formed between the upper surfaces of the valve member and the ring member during the swaging process, and thus germs cannot be mixed with fluid in the infusion route.

In the medical connector of the invention with such a configuration, since the outer diameter of the connector itself does not increase, the medical connector can be directly connected to the luer lock connector, and thus it is not necessary to use the exclusive connector.

BRIEF DESCRIPTION OF THE INVENTION

FIGS. 4A and 4B are explanatory views illustrating a method of forming the medical connector according to the invention.

FIGS. 5A, 5B, and 5C are perspective views illustrating usage examples of the medical connector according to the invention.

DESCRIPTION OF EXEMPLARY EMBODIMENTS

Hereinafter, an exemplary embodiment of the invention will be described with reference to the accompanying drawings, but the invention is not limited thereto.

Figure 1:
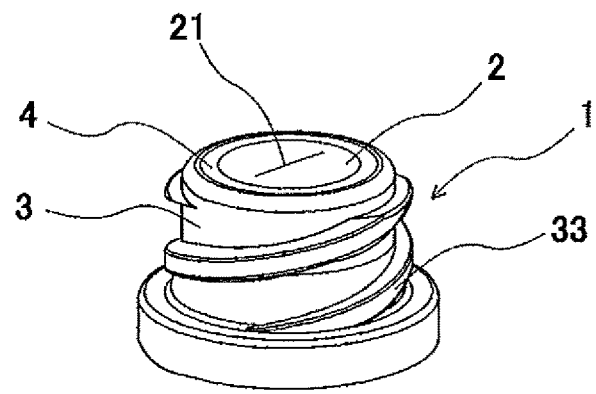
FIG. 1 is a perspective view illustrating a medical connector according to an embodiment of the invention.
Figure 2:
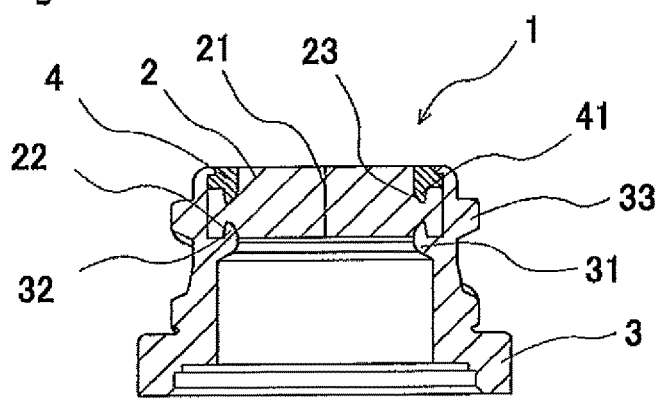
FIG. 2 is a longitudinal sectional view illustrating the medical connector shown in FIG. 1.
Figure 3:
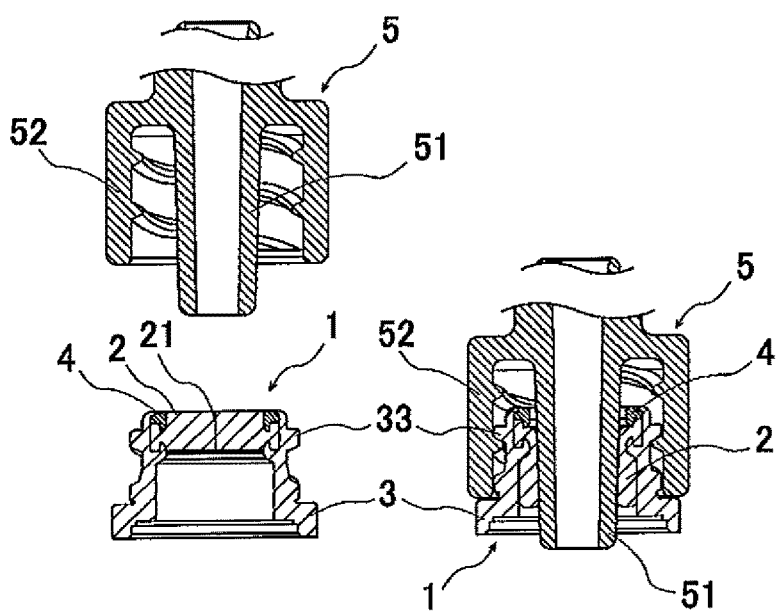
FIG. 3 is a sectional view illustrating a state where a connection tool is connected to the medical connector according to the invention.

FIG. 1 is a perspective view illustrating a medical connector according to an embodiment of the invention. FIG. 2 is a longitudinal sectional view illustrating the medical connector shown in FIG. 1. FIG. 3 is a sectional view illustrating a state where a luer lock connector is connected to the medical connector according to the invention. FIGS. 4A and 4B are explanatory views illustrating a method of forming the medical connector according to the invention. FIGS. 5A, 5B, and 5C are perspective views illustrating usage examples of the medical connector according to the invention.

As shown in FIGS. 1 and 2, a medical connector 1 according to the invention includes a disc shaped valve member 2 having a slit 21 formed at the center thereof, a housing 3 which sandwiches a circumferential edge of the valve member 2, and a ring member 4 which is disposed in the upper circumferential edge other than the center portion of the valve member 2. The valve member 2 is placed on a pedestal 31 which is formed in the inner circumferential surface of the housing 3 so as to protrude inward, and is fixed to the housing 3 by allowing the housing 3 and the ring member 4 disposed in the upper portion to be joined to each other.

The medical connector 1 according to the invention is disposed in an infusion route and allows the infusion route to internally communicate with the inside of the connection tool in such a manner that a distal end portion of a medical connection tool such as a syringe or a luer connector is inserted into the valve member 2 from the upside to thereby open the slit 21.

The disc shaped valve member 2 which is used in the medical connector 1 according to the invention is formed into a substantially cylindrical member with a diameter in the range of 5.0 to 6.5 mm and a height in the range of 1.0 to 3.0 mm. As shown in FIG. 3, when the diameter of the valve member 2 is smaller than 5.0 mm, it is difficult to insert a male luer 51 of a luer lock connector 5 having a standardized outer diameter of about 4.0 mm into the connector 1. When the diameter of the valve member 2 is larger than 6.5 mm, an outer diameter of the medical connector 1 becomes large, and thus it is difficult to connect a female screw 52 of the luer lock connector 5 to the medical connector 1. When the height of the valve member 2 is smaller than 1.0 mm, air-tightness upon inserting the connection tool into the connector 1 deteriorates, or when the height thereof is larger than 3.0 mm, it is difficult to insert the connection tool into the connector 1 because an insertion resistance of the insertion tool becomes large.

The valve member 2 is formed by a press moldings using a material that is selected from synthetic rubber such as isoprene rubber, natural rubber, silicone rubber, thermoplastic elastomer, and the like in consideration of air-tightness or resealing. In addition, a slit 21 is formed in the valve member 2 by allowing a sharp knife to pass therethrough. The slit 21 may be formed into a linear shape or a cross shape.

In addition, the valve member 2 may be provided with a groove 22 formed on a lower surface thereof so as to be fitted to the pedestal 31 of the housing 3 and an annular groove 23 formed on an upper surface thereof so as to dispose the ring member 4 described below thereon. The grooves 22 and 23 are configured to more stably fix the housing 3 or the ring member 4 to the valve member 2, and the shape thereof is not limited to that shown in the drawings, but may be appropriately modified in accordance with the shape of the ring member 4 and the pedestal 31 of the housing 3.

The housing 3 used for the medical connector 1 according to the invention is formed into a substantially cylindrical member with an inner diameter allowing the valve member 2 to be fixed to the inside thereof. It is desirable that the housing 3 has an inner diameter allowing the circumferential edge of the valve member 2 to be sandwiched in order to reseal the slit 21 of the valve member 2 fixed to the inside of the housing 3 after drawing out the connection tool inserted into the slit 21. Specifically, it is desirable that the inner diameter of the housing 3 is identical with the diameter of the valve member 2. In addition, it is desirable that the outer diameter of the housing 3 is in the range of 6.0 to 7.0 mm so that a medical luer lock connector based on ISO 594 standard can be connected thereto. When a screw portion 33 which is screw-connected to the female screw 52 of the luer lock connector 5 is formed in the outer circumferential surface of the housing 3, it is desirable that the outer diameter of the housing 3 is in the range of 7.2 to 8.0 mm.

In order to dispose the valve member 2 inside the housing 3, the pedestal 31 is formed in the inner circumferential surface of the housing 3 so as to protrude inward. In order to more stably fix the valve member 2 to the housing 3 in a state that the valve member 2 is inserted into the housing 3 to be thereby placed on the pedestal 31, it is more desirable that a protrusion 32 is formed in the upper surface of the pedestal 31 so as to protrude upward and the groove 22 is formed in the lower surface of the valve member 2 so as to correspond to the protrusion 32. The shapes of the protrusion 32 and the groove 22 are not limited, but it is desirable that the protrusion 32 and the groove 22 are formed into a ring shape.

In addition, as described above, it is desirable that a screw portion 33 is formed in the outer circumferential surface of the housing 3 so as to be screw-connected to the luer lock connector 5. As shown in FIG. 3, the luer lock connector 5 indicates the connection tool in which the female screw 52 is formed in the outer circumference of the male luer 51. The screw portion 33 is preferably a double-thread screw to which the medical luer lock connector 5 based on ISO 594 standard having a crest diameter (diameter of the thread) of 7.0±0.2 mm and a root diameter (diameter of the screw between the threads) of 8.0±0.1 mm can be connected.

It is desirable that the housing 3 is formed of material having strength for surely holding the valve member 2, and thermoplastic resin such as polypropylene, polyethylene, polycarbonate, polystyrene, or polyacetal can be preferably used as the material. The housing 3 is formed of these materials by injection molding or the like.

The ring member 4 used for the medical connector 1 according to the invention is an annular member which is disposed on the upper portion of the valve member 2 so as to fix the valve member 2 to the inside of the housing 3. Although the ring member 4 is disposed at the upper end portion of the housing 3, it is more desirable that the circumferential edge portion of the ring member 4 is sandwiched by the housing 3 in order to surely allow the upper end portion of the housing 3 to be flush with the upper surface of the ring member 4 without a stepped portion. Accordingly, it is desirable that the outer diameter of the ring member 4 is identical with the inner diameter of the upper end portion of the housing 3 and is identical or substantially the same as the outer diameter of the valve member 2. The ring member 4 is preferably formed of the same material as that of the housing, that is, a thermoplastic resin such as polypropylene, polyethylene, polycarbonate, polystyrene, or polyacetal.

In addition, since the ring member 4 is disposed on the upper circumferential edge portion of the valve member 2 other than the center portion thereof in order not to interrupt a connection operation in which the connection tool is inserted into the slit 21, it is desirable that the inner diameter is not less than 4.4 mm. When the inner diameter is smaller than 4.4 mm and then the medical luer lock connector 5 based on ISO 594 standard is inserted, there arises a problem that the male luer 51 of the luer lock connector 5 contacts with the ring member 4 to thereby damage the male luer 51, so that air-tightness during a connection deteriorates.

When the ring member 4 is disposed on the upper portion of the valve member 2, it is preferable that the ring member 4 is disposed in an annular groove 23 which is formed in the upper surface of the valve member 2 so that the upper surface of the valve member 2 is flush with the upper surface of the ring member 4. In this case, the shape and the depth of the annular groove 23 which is formed in the valve member 2 correspond to the height and the shape of the lower surface of the ring member 4. For instance, as shown in FIG. 2, a claw portion 41 with a ring shape is formed in the inner circumferential edge portion of the lower surface of the ring member 4 so as to protrude downward. Then, an annular groove 23 is formed in the outer circumferential edge portion of the upper surface of the valve member 2 so as to correspond to the claw portion 41. Accordingly, it is possible to stably dispose the ring member 4 in the valve member 2.

The ring member 4 which is disposed on the upper circumferential edge portion of the valve member 2 is joined to the upper end portion of the housing 3 by a swaging process. An exemplary joint method will be described with reference to the sectional views shown in FIGS. 4A and 4B. A concave portion 42 is formed in the outer circumferential edge of the upper surface of the ring member 4 as shown in FIG. 4A. Although the upper surface of the ring member 4 is flush with the upper surface of the valve member 2 which is disposed in the housing 3, both the upper surface of the ring member 4 and the upper surface of the valve member 2 are disposed at a position of 0 to 0.2 mm above the upper end potion of the housing 3 (shown in FIG. 4A) or at a position of 0 to 1.0 mm below the upper end portion of the housing 3 (not shown). In this state, when a swaging process is carried out by using a horn 6 having a concave portion 61 in which curve surfaces 62 are formed at both end portions, the upper end portion of the housing 3 is melted to be thereby deformed inward. Accordingly, the upper end portion is joined to the circumferential edge portion of the ring member 4. At this time, the upper end portion of the melted housing flows into the concave portion 42 which is formed in the ring member 4. Accordingly, as shown in FIG. 4B, all the upper surfaces of the housing 3, the ring member 4, and the valve member 2 are flush with one another.

As a condition of the swaging process suitable for the above-described process, a frequency of an ultrasonic vibration is about in the range of 20 to 40 kHz, an oscillation time is about 0.3 sec, and a load during the oscillation is about in the range of 20 to 100 N in a case that an ultrasonic vibration is used, but other means such as high-frequency induction heating may be used instead of the ultrasonic vibration.

One of the specific methods for producing a medical connector 1 comprises; preparing a disc shaped valve member 2 which has a slit formed at a center portion thereof; a housing 3 with a substantially cylindrical shape which sandwiches a circumferential edge portion of the valve member 2; and an annular ring member 4 which is disposed on an upper circumferential edge of the valve member 2 other than at the center portion thereof, wherein an annular groove 23 is formed in an upper surface of the valve member 2, wherein the housing 3 has a pedestal 31 which is formed in an inner circumferential surface of the housing 3 so as to protrude inward, and wherein a concave portion 42 is formed in an outer circumferential edge of the upper surface of the ring member 4, placing the valve member 2 on the pedestal 31 of the housing 3, disposing the annular ring member 4 in the annular groove 23 of the valve member 2, so that the upper surface of the valve member 2 is flush with an upper surface of the ring member 4, and the surfaces thereof are disposed at a position above an upper end portion of the housing 3, and melting the upper portion of the housing 3 to be deformed inward and flown into the concave portion 42 in the ring member 4 by swaging so that the upper surfaces of the housing 3, the ring member 4, and the valve member 2 are flush with one another to fix the valve member 2 to the housing 3.

FIGS. 5A, 5B, and 5C are views illustrating specific usage examples of the medical connector 1 according to the invention. The usage example shown in FIG. 5A indicates a plug which is connected to a plug base 7. The usage example shown in FIG. 5B indicates a T-shaped mixing/injection tube which is connected to a T-shaped tube base 8. The usage example shown in FIG. 5C indicates a three-way stopcock which is connected to a three-way stopcock base 9.

In the above-described usage examples, since the connection tool which is connected to the medical connector 1 according to the invention, that is, the luer lock connector 5 is firmly fixed to the medical connector 1 by a screw-connection operation, it is not necessary to maintain the connection state by using other components. Alternatively, it is not necessary for a user to maintain the medical connector 1 so as to maintain the connection state. As a result, this advantage is particularly apparent in the three-way stopcock shown in FIG. 5C, and thus it is possible to operate the three-way stopcock without maintaining the connection state after the connection of the connection tool.

What is claimed is:

1. A medical connector having a substantially cylindrical shape and having a first upper end for receiving a male luer and a second lower end, said medical connector comprising:

a valve arranged at the first upper end of said medical connector, the valve consisting of an elastomeric disc having an uppermost surface and a lowermost surface, a slit formed at a center portion thereof, an upper groove formed in a circumferential edge portion of the uppermost surface, and a lower groove formed in a circumferential edge portion of the lowermost surface;

a housing with a substantially cylindrical shape having a pedestal for supporting the valve;

a protrusion projecting upwardly from the pedestal, and being arranged in the lower groove of the valve such that the protrusion is disposed between a radially center portion and a radially outer rim portion of the valve in a lower side of the valve;

and an annular ring member which is disposed on the circumferential edge portion of the uppermost surface of the valve other than the center portion thereof, and having a claw portion integrally formed at a radially inner portion thereof so as to project downwardly, the claw portion being arranged in the upper groove formed on the circumferential edge portion of the uppermost surface of the valve such that the claw portion is disposed between the radially center portion and the radially outer rim portion of the valve in an upper side of the valve wherein the valve is fixed to the housing by joining of the annular ring member and the housing to each other.

2. The medical connector according to claim 1, wherein a screw portion is formed in an outer circumferential surface of the housing so as to be screw-connected to a luer lock connector.

3. The medical connector according to claim 1, wherein the outer diameter of the ring member is the same as the outer diameter of the valve.

4. The medical connector according to claim 1, wherein the annular ring member and the housing are joined to each other by melting the housing.

5. The medical connector according to claim 4, wherein the melting is by ultrasonic vibration.

* * * * *